US00PP36194P2

(12) United States Plant Patent
Heuger

(10) Patent No.: US PP36,194 P2
(45) Date of Patent: Oct. 8, 2024

(54) ***HELLEBORUS* PLANT NAMED 'HG 1426'**

(50) Latin Name: ***Helleborus ericsmithii* X *Helleborus* x *hybridus***
Varietal Denomination: HG 1426

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 18/389,563

(22) Filed: Nov. 14, 2023

(51) Int. Cl.
*A01H 5/02* (2018.01)
*A01H 6/72* (2018.01)

(52) U.S. Cl.
USPC ..... Plt./439

(58) Field of Classification Search
USPC ..... Plt./263.1, 439
See application file for complete search history.

*Primary Examiner* — Karen M Redden
(74) *Attorney, Agent, or Firm* — C. Anne Whealy

(57) ABSTRACT

A new and distinct cultivar of *Helleborus* plant named 'HG 1426', characterized by its upright to somewhat outwardly spreading and mounded plant habit; moderately vigorous to vigorous growth habit; dark green-colored leaflets with lighter green-colored venation; freely flowering habit; greenish white-colored flowers; and good garden performance.

1 Drawing Sheet

Figure 1:
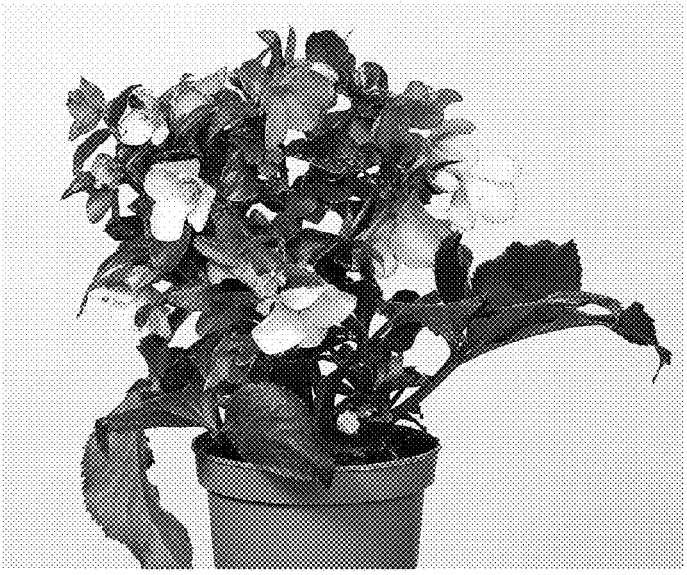

Botanical designation: *Helleborus ericsmithii* X *Helleborus* x *hybridus.*

Cultivar denomination: 'HG 1426'.

STATEMENT REGARDING PRIOR DISCLOSURES BY INVENTOR/APPLICANT

An European Community Plant Breeder's Rights application for the instant plant was filed by the Inventor/Applicant, Mr. Josef Heuger of Glandorf, Germany, on Dec. 1, 2022, application number 2022/2744. Foreign priority is not claimed to this application.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor or Applicant. Inventor/Applicant claims a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Helleborus* plant, botanically known as *Helleborus ericsmithii* X *Helleborus* x *hybridus* and hereinafter referred to by the name 'HG 1426'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stresses.

The new *Helleborus* plant is a naturally-occurring whole plant mutation of *Helleborus ericsmithii* X *Helleborus* x *hybridus* 'COSEH 4000', disclosed in U.S. Plant Pat. No. 28,294. The new *Helleborus* plant was discovered and selected by the Inventor as a single flowering plant from within a population of plants of 'COSEH 4000' in a controlled greenhouse environment in Glandorf, Germany in October, 2018.

Asexual reproduction of the new *Helleborus* plant by in vitro axillary meristem culture in a controlled environment in Glandorf, Germany since April, 2019 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HG 1426'. These characteristics in combination distinguish 'HG 1426' as a new and distinct *Helleborus* plant:

1. Upright to somewhat outwardly spreading and mounded plant habit.
2. Moderately vigorous to vigorous growth habit.
3. Dark green-colored leaflets with lighter green-colored venation.
4. Freely flowering habit.
5. Greenish white-colored flowers.
6. Good garden performance.

Plants of the new *Helleborus* differ from plants of the mutation parent, 'COSEH 4000', in the following characteristics:

1. Plants of the new *Helleborus* have smaller flowers than plants of 'COSEH 4000'.
2. Flowers of plants of the new *Helleborus* are greenish white in color whereas flowers of plants of 'COSEH 4000' are white in color with red purple-colored margins.

Plants of the new *Helleborus* can also be compared to plants of *Helleborus* x *ericsmithii* X *Helleborus* x *hybridus* 'COSEH 4100', disclosed in U.S. Plant Pat. No. 28,296. In side-by-side comparisons, plants of the new *Helleborus* differ primarily from plants of 'COSEH 4100' in flower color as flowers of plants of the new *Helleborus* are greenish white in color whereas flowers of plants of 'COSEH 4100' are red purple to greyed purple in color.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph at the top of the sheet (FIG. 1) is a side perspective view of a typical flowering plant of 'HG 1426' grown in a container.

Figure 2:
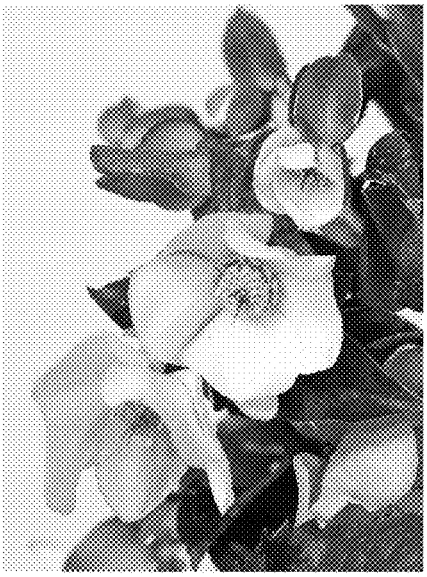

The photograph at the bottom of the sheet (FIG. 2) is a close-up view of a typical flowering plant of 'HG 1426'.

DETAILED BOTANICAL DESCRIPTION

The aforementioned photographs and following observations, measurements and values describe plants grown during the autumn in 17-cm containers in a glass-covered greenhouse in Glandorf, Germany and under cultural practices typical of commercial *Helleborus* production. During the production of the plants, day temperatures ranged from 12C to 32C and night temperatures ranged from 5C to 12C. Plants were 48 weeks old when the photographs were taken and 14 months old when the description was taken. In the following description, color references are made to The Royal Horticultural Society Colour Chart, 2015 Edition, except where general terms of ordinary dictionary significance are used.

Botanical classification: *Helleborus ericsmithii* X *Helleborus* x *hybridus 'HG* 1426'.

Parentage: Naturally-occurring whole plant mutation of *Helleborus ericsmithii* X *Helleborus* x *hybridus* 'COSEH 4000', disclosed in U.S. Plant Pat. No. 28,294.

Propagation:

*Type.*—In vitro axillary meristem culture.

*Time to initiate roots, winter.*—About 55 days at temperatures about 12C.

*Time to produce a rooted young plant, winter.*—About 170 days at temperatures ranging from about 4C to 15C.

*Root description.*—Thick to thin, fleshy; typically white to brownish in color, actual color of the roots is dependent on substrate composition, water quality, fertilizer type and formulation, substrate temperature and physiological age of roots.

*Rooting habit.*—Low branching; sparse.

Plant description:

*Plant and growth habit.*—Herbaceous perennial; upright to somewhat outwardly spreading and mounding plant habit with flowers held slightly above the foliar plane; plant shape, roughly flattened globular; moderately vigorous to vigorous growth habit and moderate growth rate.

*Plant height, soil level to top of foliar plane.*—About 18.9 cm.

*Plant height, soil level to top of flowers.*—About 29.3 cm.

*Plant diameter* (*area of spread*).—About 42.5 cm.

Leaf description:

*Arrangement.*—Leaves arranged in a basal rosette; leaves palmately compound with typically five leaflets per leaf.

*Leaf length.*—About 18.2 cm.

*Leaf width.*—About 22.8 cm.

*Leaflet length.*—About 14.7 cm.

*Leaflet width.*—About 6.5 cm.

*Leaf shape.*—Palmate; roughly reniform in outline.

*Leaflet shape.*—Ovate to elliptic.

*Leaflet apex.*—Acute.

*Leaflet base.*—Attenuate.

*Leaflet margin.*—Coarsely serrate; moderately coarsely undulate.

*Leaflet texture and luster, upper surface.*—Smooth, glabrous; coriaceous and tough; moderately glossy.

*Leaflet texture and luster, lower surface.*—Smooth, glabrous; coriaceous and tough; slightly glossy.

*Leaflet venation pattern.*—Pinnate and reticulate.

*Leaflet color.*—Developing leaflets, upper surface: Close to 137B; at the base, slightly tinged with close to 178A. Developing leaflets, lower surface: Close to 148A to 148B; venation, close to 178A. Fully developed leaflets, upper surface: Darker than a blend of 139A and N189A; at the base, slightly tinged with close to 177A; venation, close to 145A. Fully developed leaflets, lower surface: Close to 147B; venation, close to 152A to 152B.

*Petioles.*—Length: About 12 cm. Diameter: About 6 mm by 8 mm. Strength: Strong. Texture and luster, upper and lower surfaces: Smooth, glabrous; moderately glossy. Color, upper and lower surfaces: Close to 146B; sparsely to moderately covered with fine dots, close to 1771.

Flower description:

*Flower shape and habit.*—Single rotate bowl-shaped flowers arranged in panicles; freely flowering habit with about 8 to 56 flowers per inflorescence and about 70 flowers and flower buds per plant; flowers face mostly outwardly to nodding.

*Fragrance.*—None detected.

*Natural flowering season.*—Plants begin flowering about ten months after planting; plants flower naturally during the late autumn into the winter in Germany.

*Flower longevity on the plant.*—About ten days; sepals persistent, other flower parts are not persistent.

*Flower buds.*—Length: About 1.6 cm. Diameter: About 1 cm. Shape: Ovate. Texture and luster: Smooth, glabrous; matte. Color: Close to 150C; towards the apex, tinged with close to 181A to 181B.

*Inflorescence height* (*including peduncle*).—About 29 cm.

*Inflorescence diameter.*—About 23.9 cm.

*Flower diameter.*—About 7.1 cm.

*Flower depth.*—About 3.7 cm.

*Petals.*—All petals are transformed into nectaries.

*Sepals.*—Quantity and arrangement: About five, arranged in a single whorl. Length: About 4 cm. Width: About 3.1 cm. Shape: Broadly elliptic; slightly concave. Apex: Broadly and bluntly acute to obtuse. Base: Broadly attenuate to cuneate. Margin:

Entire; coarsely undulate. Texture and luster, upper and lower surfaces: Smooth, glabrous; matte. Color: When opening, upper surface: Close to 155A and 145B. When opening, lower surface: Close to 155A, NN155B and 186B. Fully opened, upper surface: Close to 155A and a blend of 157A, 150D and 145A; venation, similar to lamina; color does not change with subsequent development. Fully opened, lower surface: Close to a blend of 155A and 150D, 145A to 145C and 178A; venation, similar to lamina; color does not change with subsequent development.

*Flower bracts.*—Quantity per flower: Typically one or two. Length: About 9.1 cm. Width: About 4.1 cm. Shape: Ovate to oblong. Apex: Acute to three-lobed. Base: Truncate to cuneate. Margin: Proximally, entire; distally, serrate; coarsely undulate. Color, upper surface: Slightly darker than a blend of 139A and 147A; towards the base, close to 146D. Color, lower surface: Close to 147B.

*Peduncles.*—Length: About 21.5 cm. Diameter: About 7 mm to 10 mm. Aspect: About 15 degrees from vertical. Strength: Strong. Texture and luster: Smooth, glabrous; matte. Color: Close to 145A; slightly to heavily covered with fine dots, close to 178B.

*Pedicels.*—Length: About 3.2 cm. Diameter: About 3 mm. Aspect: About 25 degrees from peduncle axis. Strength: Moderately strong. Texture and luster: Smooth, glabrous; moderately glossy. Color: Close to 146D; sparsely to moderately covered with fine dots, close to 177A.

*Reproductive organs.*—Stamens: Quantity per flower: About 90. Filament length: About 1.7 cm. Filament color: Close to 150D. Anther shape: Double and broadly reniform; basifixed. Anther size: About 2 mm by 2.75 mm. Anther color: Close to 154C. Pollen amount: Sparse to moderate. Pollen color: Close to 4D to lighter than 4D. Pistils: Quantity per flower: About five to eight. Pistil length: About 1.1 cm. Stigma diameter: About 0.3 mm. Stigma shape: Club-shaped. Stigma color: Close to 151D. Style length: About 1.05 cm. Style color: Close to 185D. Ovary color: Close to 145B. Nectaries (transformed petals): Quantity per flower: About 13. Length: About 1 cm. Diameter: About 3.5 mm. Shape: Tubular, flattened; apices, obtuse. Texture and luster, inner and outer surfaces: Smooth, glabrous; slightly glossy. Color, immature, inner and outer surfaces: Close to 144A; towards the apex, close to 153C to 153D. Color, mature, inner and outer surfaces: Close to N144A; towards the apex, close to 153B; venation, similar to lamina color; with subsequent development, color becoming closer to 146C to 146D and distally, close to 14B.

*Seeds and fruits.*—To date, seed and fruit development have not been observed on plants of the new *Helleborus.*

Garden performance: Plants of the new *Helleborus* have been observed to have good garden performance and to tolerate rain, wind, high temperatures about 35C and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'HG 1426' as illustrated and described.

* * * * *